United States Patent [19]

Mitsui et al.

[11] Patent Number: 4,861,766

[45] Date of Patent: Aug. 29, 1989

[54] ANTIMICROBIAL COMPOSITION

[75] Inventors: Susumu Mitsui; Shigeru Kurose; Hiroshi Saimoto, all of Saitama, Japan

[73] Assignee: Takeda Chemical Industries, Ltd., Osaka, Japan

[21] Appl. No.: 946,506

[22] Filed: Dec. 19, 1986

[30] Foreign Application Priority Data

Dec. 23, 1985 [JP] Japan .................. 60-287930

[51] Int. Cl.$^4$ ............... A01N 55/02; A01N 46/06
[52] U.S. Cl. .................... 514/184; 514/446
[58] Field of Search ............ 514/372, 446, 365, 184

[56] References Cited

U.S. PATENT DOCUMENTS

| | | | |
|---|---|---|---|
| 2,957,887 | 10/1960 | Berkey et al. | 260/332.1 |
| 3,862,323 | 1/1975 | Brink et al. | 424/446 |
| 3,879,536 | 4/1975 | Myers, Jr. | 514/446 |
| 3,928,198 | 12/1975 | Brink, Jr. et al. | 514/446 |
| 3,929,561 | 12/1975 | Shema et al. | 162/161 |
| 4,150,026 | 4/1979 | Miller et al. | 260/299 |
| 4,396,413 | 8/1983 | Miller et al. | 514/184 |

*Primary Examiner*—Douglas W. Robinson
*Assistant Examiner*—Raymond J. Henley, III
*Attorney, Agent, or Firm*—Wenderoth, Lind & Ponack

[57] ABSTRACT

An antimicrobial composition containing, as a mixture of active ingredients, (A) at least one complex of the formula

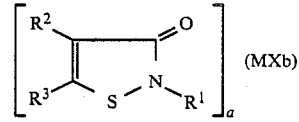

(MXb)

wherein $R^1$ is a hydrogen atom or a substituted or unsubstituted monovalent hydrocarbyl group, $R^2$ and $R^3$ are each independently a hydrogen atom or a halogen atom, M is a metal or ammonium cation, X is a complex-forming anion, a is 1 or 2 and b is an integer which is such that the anion X satisfies the valence of the cation M, and (B) 3,3,4,4-tetrachlorotetrahydrothiophene 1,1-dioxide effectively inhibits the growth of microbes in, for example, industrial water systems for pulp and paper.

6 Claims, No Drawings

ANTIMICROBIAL COMPOSITION

This invention relates to a novel antimicrobial composition which contains an isothiazolone complex or isothiazolone derivative complex of general formula (I) and 3,3,4,4-tetrachlorotetrahydrothiophene 1,1-dioxide (hereinafter sometimes referred to as "compound (II)") and in which full advantage is taken of the synergism between both the active ingredients. This antimicrobial composition is suited particularly for use in industrial water systems in pulp and paper manufacture.

In wastewater from the papermaking process in the field of paper and pulp industry and in various water systems in various fields of industry, such as in circulating cooling water, and further in water-based paints, sizing liquids for paper, latices, printing pastes, leathers and like products manufactured by using industrial water, harmful microorganisms can grow with ease to cause decrease in productivity and/or quality of products. In water systems in the paper and pulp industry, in particular, the growth and proliferation of bacteria, filamentous microorganisms and yeasts lead to the formation of slime. In watercourses in which the pulp slurry flows, in particular at places having a rough wall surface which comes into contact with the slurry and at places where the pulp slurry decreases in flow rate and becomes stagnant, for example in the chest, flow box and transportation pipe, slime formation and adherence take place. This slime often detaches and causes paper breakage and/or contamination of paper and pulp products. The growth of microorganisms in slime also causes various other troubles.

Where the papermaking machines operate at high-speed these troubles present very serious problems, provoking marked decrease in productivity and significant economic losses.

Also in circulating cooling water systems for metal cutting oils, microorganisms can grow and proliferate to thereby affect the cooling power and/or emulsifiability of the cutting oils adversely or cause phenomena unfavorable from the public health viewpoint through bad odor emission and/or impairment of the working environment. Troubles caused by the growth of harmful microorganisms are also encountered in industrial products such as water-based paints, sizing liquids for paper, polymer latices, pulp for papermaking, pastes, leathers, and metal cutting oils.

Those agents which have been so far in use for the inhibition or prevention of growth of harmful microorganisms in the above-mentioned water systems or in the above-mentioned industrial products include, among others, organometallic compounds, organochlorine compounds, organosulfur compounds and quaternary ammonium compounds. These compounds, however, are toxic to humans, have unpleasant or offensive odor and, furthermore, may cause unfavorable phenomena such as foaming. In addition, water systems containing these agents, when discharged into ordinary rivers or watercourses or into the sea, may adversely affect aquatic animals and thus pose problems from the environmental protection viewpoint.

The present inventors conducted intensive investigations in an attempt to eliminate the above-mentioned drawbacks and, as a result, have now completed the present invention.

Thus, this invention provides an antimicrobial composition specified below:

An antimicrobial composition which contains, as a mixture of active ingredients, (A) at least one complex of the formula

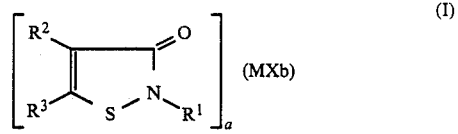

wherein $R^1$ is a hydrogen atom or a substituted or unsubstituted monovalent hydrocarbyl group, $R^2$ and $R^3$ are each independently a hydrogen atom or a halogen atom, M is a metal or ammonium cation, X is a complex-forming anion, a is 1 or 2 and b is an integer which is such that the anion X satisfies the valence of the cation M, and (B) 3,3,4,4-tetrachlorotetrahydrothiophene 1,1-dioxide.

Some of the complexes of general formula (I) are the complexes described in U.S. Pat. No. 4,150,026 whereas the compound (II) is also a bactericide described in U.S. Pat. No. 2,957,887. The complexes of general formula (I) and the compound (II) can be produced in a manner analogous to known methods.

These bactericides separately are still unsatisfactory as antimicrobial agents, for example in that they are effective against only limited kinds of microorganism. Hence they produce insufficient bactericidal effect, and fail to retain their effect for a prolonged period of time.

The antimicrobial composition according to the invention can produce a very high antimicrobial effect which could have never been expected from the experience with each individual constituent active ingredient. Furthermore, it has a broad range of applications against harmful microorganisms, namely filamentous bacteria, other bacteria, yeasts, fungi, and so forth, irrespective of species thereof.

As for the complexes of the general formula (I), metal cations represented by M and complex-forming anions represented by X include respectively the corresponding metal cations and anions described in the above-mentioned U.S. Pat. No. 4,150,026, namely metal cations such as barium, cadmium, calcium, chromium, cobalt, copper, iron, lead, lithium, manganese, mercury, nickel, sodium, silver, strontium, tin, zinc or the like and anions such as chloride, bromide, iodide, sulfate, nitrate, acetate, perchlorate, bisulfate, bicarbonate, oxalate, maleate, p-toluene-sulfonate, carbonate, phosphate, and the like. As more preferred examples of M, there are mentioned cations of metals of valence of 2.

As the complex of general formula (I) which is to be used in accordance with the invention, there may be included, for example, compounds wherein $R^1$ is a $C_{1-10}$ alkyl group, $R^2$ and $R^3$ are each independently a hydrogen atom or a halogen atom, M is zinc, calcium, copper or magnesium, and X is a mineral acid anion such as chloride, bromide, nitrate or sulfate. Preferably, there may be mentioned, for example, 5-chloro-2-methyl-3-isothiazolone-magnesium nitrate, 2-methyl-3-isothiazolone-magnesium nitrate, 2-octyl-5-chloro-3-isothiazolone-calcium chloride and 2-octyl-4-chloro-3-isothiazolone-calcium chloride.

Such compounds of general formula (I) may be used either singly or in admixture of two or more of them. The compound of general formula (I) and the compound (II) are used generally in a weight ratio of 1/10 to 10/1, preferably 1/5 to 5/1.

A satisfactory effect as seen from the practical viewpoint can be achieved in the above ratio.

Basically, the antimicrobial composition according to the invention is prepared by admixing the above-mentioned two ingredients to form a homogeneous composition. Generally, however, the composition is submitted to use in the form of a solution in solvents or an emulsion or dispersion, for instance.

As the solvent usable for this purpose, there may be mentioned alcohol type solvents (e.g. methyl alcohol, ethyl alcohol, ethylene glycol, diethylene glycol), ketone type solvents,(e.g. acetone, methylethyl ketone), ether type solvents (e.g. dioxane, tetrahydrofuran) and hydrocarbon type solvents (e.g. benzene, toluene), among others. The antimicrobial composition according to the present invention may also be used in a carrier-borne form. The liquid carriers include, for example, the above-mentioned alcohols, ketones and hydrocarbons. As the solid carrier, for example, there may be mentioned clays (e.g. Kaolin, bentonite), talcs and silicas (e.g. diatomaceous soil). Thus the mode of application is not critical but various modes of application can be employed. The solvents and carriers may be conventional.

While the dose of the antimicrobial composition may vary depending on the concentration of the microorganisms, the composition is used generally in a dose of 0.01 to 100 ppm, based on the amount of the composition, in the case of water systems in the field of paper and pulp industry and the like, and 1 to 500 ppm, based on the amount of the composition, in the fields of water-based paints, pastes, leathers and the like.

The antimicrobial composition according to the invention may justifiably contain conventional additives or auxiliaries, such as stabilizers (e.g. magnesium nitrate, magnesium chloride, calcium chloride, sodium alginate) and surfactants (e.g. alkyl sulfates, polyethyleneglyco alkyl ethers,), so long as they do not lead to failure to achieve the objects of the invention. While the amount of such additives and auxiliaries to be incorporated may vary depending n the amount of active ingredients (I) and (II) to be used, the additives and auxiliaries are preferably incorporated in a 0.5 to 10 weight percent based on the composition.

There will be mentioned Examples and Comparative Examples below. The examples are intended to illustrate this invention in further detail and should by no means be construed as limiting the scope of the present invention.

Antimicrobial compositions were prepared according to the following formulations. In the examples, "part(s)" invariably means "part(s)" by weight.

EXAMPLE 1

| | |
|---|---|
| Compound (II) | 10 parts |
| 3:1 (by weight) Mixture of 5-chloro-2-methyl-3-isothiazolone-magnesium nitrate and 2-methyl-3-isothiazolone-magnesium nitrate | 10 parts |
| Diethylene glycol | 78 parts |
| Sorpol 900A (Toho Chemical) | 2 parts |

The above-mentioned ingredients were admixed in the specified amount homogeneously to give a composition.

EXAMPLE 2

An antimicrobial composition was prepared from the ingredients given below in the same manner as in Example 1.

| | |
|---|---|
| Compound (II) | 10 parts |
| 5-Chloro-2-octyl-3-isothiazolone-calcium (II) chloride | 10 parts |
| Diethylene glycol | 78 parts |
| Sorpol 900A | 2 parts |

COMPARATIVE EXAMPLE 1

An antimicrobial composition was prepared from the ingredients given below in the same manner as in Example 1.

| | |
|---|---|
| Compound (II) | 20 parts |
| Diethylene glycol | 78 parts |
| Sorpol 900A | 2 parts |

COMPARATIVE EXAMPLE 2

An antimicrobial composition was prepared from the ingredients given below in the same manner as in Example 1.

| | |
|---|---|
| 3:1(by weight) Mixture of 5-chloro-2-methyl-3-isothiazolone-magnesium (II) nitrate and 2-methyl-3-isothiazolone-magnesium (II) nitrate | 20 parts |
| Diethylene glycol | 80 parts |

COMPARATIVE EXAMPLE 3

An antimicrobial composition was prepared from the ingredients given below in the same manner as in Example 1.

| | |
|---|---|
| 5-Chloro-2-octyl-3-isothiazolone-calcium (II) chloride | 20 parts |
| Diethylene glycol | 78 parts |
| Sorpol 900A | 2 parts |

The antimicrobial compositions prepared in the above Examples 1 to 2 and Comparative Examples 1 to 3 were tested for their effects in slime control and preservation.

TEST EXAMPLE 1

Inhibition of microbial growth and control of slime formation in the papermaking process.

In the papermaking process in a certain paper mill, the antimicrobial compositions prepared in the above Examples 1 to 2 and Comparative Examples 1 to 3 were separately added to a white water pit three times a day, each time for 2 hours, to a concentration in water of 20 ppm, based on the amount of the composition. After 7 days of such addition, the number of the microorganisms in white water was counted.

For the counting, a white water sample taken was diluted with sterile water, a known amount of the dilution was placed in a dish, a Waksman agar medium solution was poured into the dish, and the mixture was homogenized and then allowed to solidify in a plate form. After 2 days of cultivation in an incubator (32° C.), the microbial colonies formed were counted using a colony counter. The frequency of paper breakage during the papermaking process was also recorded for further confirmation of the bactericidal effect. The results of these tests are shown below in Table 1.

TABLE 1

|  | Microbial count in white water (cells/ml) | Frequency of paper breakage (times) |
|---|---|---|
| Example 1 | $<10^2$ | 0 |
| Example 2 | $<10^2$ | 0 |
| Comparative Example 1 | $2.1 \times 10^4$ | 7 |
| Comparative Example 2 | $3.4 \times 10^3$ | 5 |
| Comparative Example 3 | $6.8 \times 10^3$ | 6 |
| No addition of bactericide | $\geq 10^8$ | 15 |

The data given in Table 1 indicate that the antimicrobial compositions according to the invention (Examples 1 to 2) have an excellent microbial growth inhibiting activity.

TEST EXAMPLE 2

Inhibition of microbial growth in a sizing composition for papermaking.

To a starch-based sizing liquid having a pH of 10.0, there were added a bouillon liquid medium and a preliminarily rotten sizing liquid. The mixture was stirred and each of the antimicrobial compositions prepared in the above Examples and Comparative Examples was added respectively to a concentration of 300 ppm, based on the amount of the composition.

After 5 days' maintenance of the mixture in an incubator at 32° C., the viable count in each sizing liquid was conducted. The results thus obtained are shown below in Table 2.

TABLE 2

|  | Viable microbe cell number (cells/ml) |
|---|---|
| Example 1 | $<10^2$ |
| Example 2 | $<10^2$ |
| Comparative Example 1 | $2.5 \times 10^6$ |
| Comparative Example 2 | $8.0 \times 10^3$ |
| Comparative Example 3 | $7.6 \times 10^3$ |
| No addition of bactericide | $7.6 \times 10^8$ |

What we claim:

1. An antimicrobial composition comprising, as a mixture of active ingredients, (A) one or two complexes of the formula

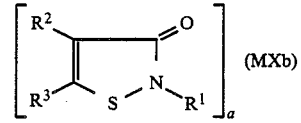

wherein $R^1$ is hydrogen or $C_{1-10}$ alkyl, $R^2$ and $R^3$ are each independently hydrogen or halogen, M is a metal having a valence of 2, X is a complex-forming anion, a is 1 or 2 and b is an integer which is such that the anion X satisfies the valence of the metal M, and (B) 3,3,4,4-tetrachlorotetrahydrothiophene 1,1-dioxide, wherein the complex and 3,3,4,4-tetrachlorotetrahydrothiophene 1,1-dioxide are contained in the mixture in a weight ratio 1/10 to 10/1.

2. An antimicrobial composition as claimed in claim 1, wherein the metal represented by M is zinc, magnesium, calcium or copper.

3. An antimicrobial composition as claimed in claim 1, wherein the complex is 5-chloro-2-methyl-3-isothiazolone-magnesium nitrate.

4. An antimicrobial composition as claimed in claim 1, wherein the complex is 2-methyl-3-isothiazolone-magnesium nitrate.

5. An antimicrobial composition as claimed in claim 1, wherein as the active ingredient (A), an admixture of 5-chloro-2-methyl-3-isothiazolone-magnesium nitrate and 2-methyl-3-isothiazolone-magnesium nitrate in a weight ratio of 3 to 1 is used.

6. An antimicrobial composition as claimed in claim 1 wherein the complex is 2-octyl-5-chloro-3-isothiazolone-calcium chloride.

* * * * *